United States Patent
Nakamura et al.

(10) Patent No.: US 8,335,361 B2
(45) Date of Patent: Dec. 18, 2012

(54) MEDICAL IMAGE PROCESSING APPARATUS AND MEDICAL IMAGE PROCESSING METHOD

(75) Inventors: Kenji Nakamura, Chiba (JP); Hideki Tanaka, Tama (JP); Hirokazu Nishimura, Hachioji (JP); Ryoko Inoue, Hachioji (JP); Miho Sawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1132 days.

(21) Appl. No.: 12/209,567

(22) Filed: Sep. 12, 2008

(65) Prior Publication Data

US 2009/0074271 A1    Mar. 19, 2009

Related U.S. Application Data

(63) Continuation of application No. PCT/JP2007/053586, filed on Feb. 27, 2007.

(30) Foreign Application Priority Data

Mar. 15, 2006   (JP) ................................. 2006-071197

(51) Int. Cl.
*G06K 9/00*   (2006.01)
(52) U.S. Cl. ....................................... 382/128; 382/285
(58) Field of Classification Search .................. 382/128, 382/285
See application file for complete search history.

(56) References Cited

U.S. PATENT DOCUMENTS

| 5,079,698 | A | 1/1992 | Grenier et al. |
|---|---|---|---|
| 5,764,809 | A | 6/1998 | Nomami et al. |
| 6,529,618 | B1 | 3/2003 | Ohara et al. |
| 2003/0228064 | A1 | 12/2003 | Gindele et al. |
| 2004/0151379 | A1* | 8/2004 | Kim et al. ..................... 382/209 |
| 2005/0001832 | A1 | 1/2005 | Shen et al. |
| 2007/0197865 | A1* | 8/2007 | Miyake et al. ................ 600/109 |

FOREIGN PATENT DOCUMENTS

| CN | 1663531 A | 9/2005 |
|---|---|---|
| EP | 0 984 393 A2 | 3/2000 |
| EP | 1 437 083 A1 | 7/2004 |
| JP | 02-224745 | 9/1990 |
| JP | 05-108819 | 4/1993 |
| JP | 08-029701 | 2/1996 |
| JP | 10-210454 | 8/1998 |
| JP | 2000-079109 | 3/2000 |
| JP | 2000-126162 | 5/2000 |

OTHER PUBLICATIONS

European Office Action dated Nov. 24, 2011 from corresponding European Patent Application Publication No. EP 07 714 979.7.
Extended Supplementary European Search Report dated Jul. 22, 2010.
Chinese Official Action dated Feb. 5, 2010.

\* cited by examiner

*Primary Examiner* — Phat X Cao
(74) *Attorney, Agent, or Firm* — Scully, Scott, Murphy & Presser, P.C.

(57) ABSTRACT

A medical image processing apparatus which performs image processing on a medical input image, includes: a pixel extraction portion for extracting an inappropriate pixel satisfying a predetermined condition in the input image, a replacing pixel information calculation portion for calculating replacing information with which pixel information of the inappropriate pixel is to be replaced, based on pixel information of a predetermined region including the extracted inappropriate pixel or adjacent to the extracted inappropriate pixel and a replaced image generation portion for replacing the pixel information of the inappropriate pixel in the input image with the replacing information and generating a replaced image.

5 Claims, 7 Drawing Sheets

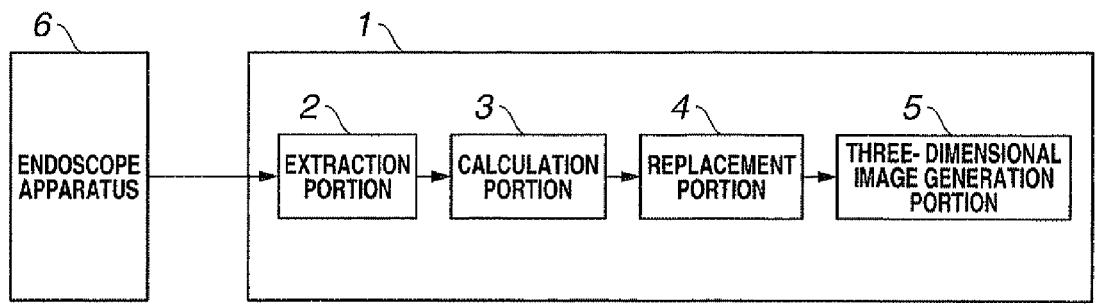
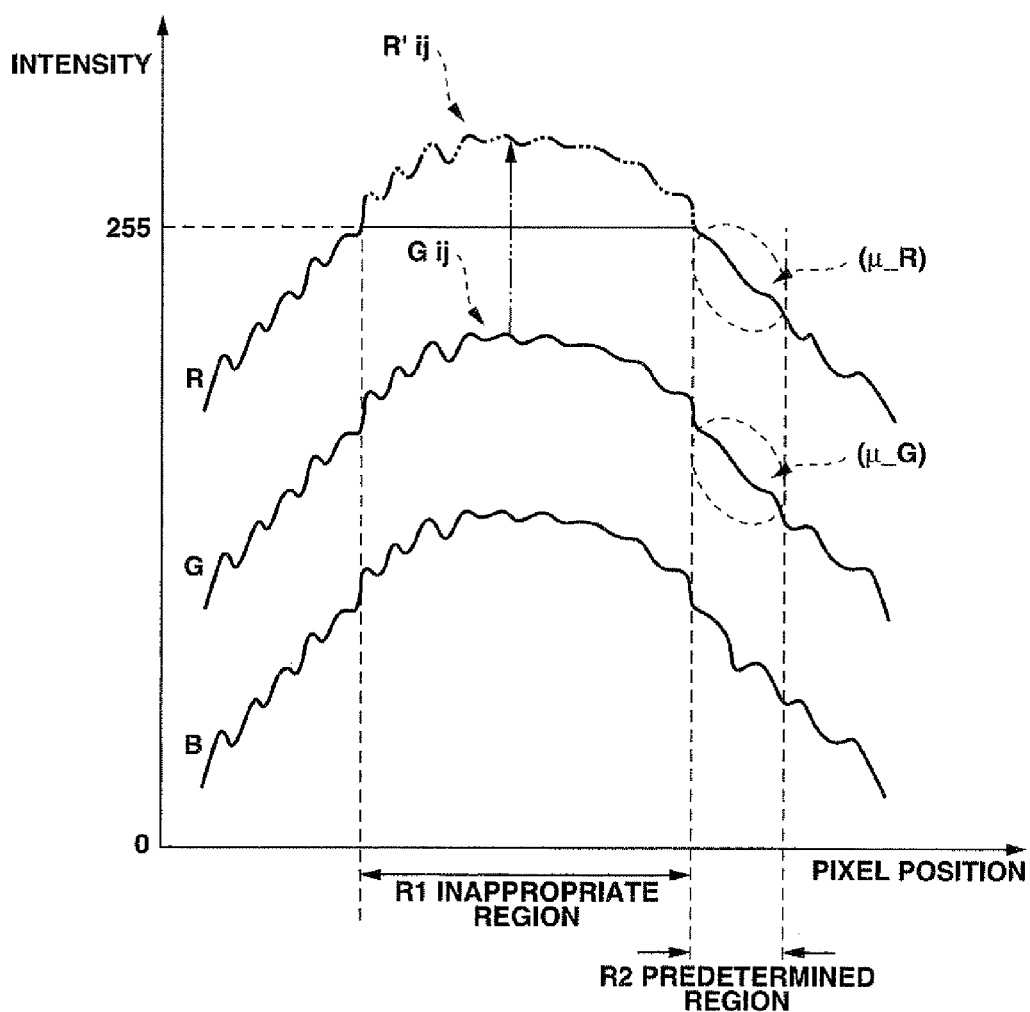

MEDICAL IMAGE PROCESSING APPARATUS AND MEDICAL IMAGE PROCESSING METHOD

CROSS REFERENCE TO RELATED APPLICATION

This application is a continuation application of PCT/JP2007/053586 filed on Feb. 27, 2007 and claims benefit of Japanese Application No. 2006-071197 filed in Japan on Mar. 15, 2006, the contents of which are incorporated herein by this reference.

BACKGROUND OF INVENTION

1. Field of the Invention

The present invention relates to a medical image processing apparatus and a medical image processing method for performing image processing on a medical input image.

2. Description of the Related Art

In a field of medicine, observation and diagnosis of an organ in a body cavity using a medical instrument having an image pickup function have been widely performed. In a medical instrument having an image pickup function such as an endoscope apparatus, an elongated insertion portion is inserted into a body cavity, and an image of an organ in the body cavity is picked up by image pickup means provided at a distal end portion of the insertion portion. A surgeon performs observation and diagnosis from an endoscope image obtained by image pickup.

Endoscope images may be subjected to image processing such as color enhancement which improves visibility at diagnosis by an image processing apparatus or the like. An endoscope image obtained by image pickup, however, may include a halation portion, dark portion, or the like, and an accurate image processing result may not be obtained.

For the reason, an image processing apparatus which appropriately removes image data of a portion such as a halation portion or dark portion from which an accurate image processing result is not obtained such that image processing is accurately performed is proposed in Japanese Patent Application Laid-Open Publication No. 10-210454.

SUMMARY OF THE INVENTION

A medical image processing apparatus according to the present invention is a medical image processing apparatus which performs image processing on a medical input image, includes: a pixel extraction portion for extracting an inappropriate pixel satisfying a predetermined condition in the input image, a replacing pixel information calculation portion for calculating replacing information with which pixel information of the inappropriate pixel is to be replaced, based on pixel information of a predetermined region including the extracted inappropriate pixel or adjacent to the extracted inappropriate pixel, and a replaced image generation portion for replacing the pixel information of the inappropriate pixel in the input image with the replacing information and generating a replaced image.

A medical image processing method according to the present invention is a medical image processing method for performing image processing on a medical input image, includes: a pixel extraction step of extracting an inappropriate pixel satisfying a predetermined condition in the input image, a replacing pixel information calculation step of calculating replacing information with which pixel information of the inappropriate pixel is to be replaced, based on pixel information of a predetermined region including the extracted inappropriate pixel or adjacent to the extracted inappropriate pixel, and a replaced image generation step of generating a replaced image obtained by replacing the pixel information of the inappropriate pixel in the input image with the calculated replacing information.

BRIEF DESCRIPTION OF THE DRAWINGS

FIG. 1 is a diagram of a schematic configuration of an image processing apparatus according to a first embodiment;

FIG. 2 is a graph showing an example of a relationship between R, G, and B signal intensity values and a pixel position in a picked-up image according to the first embodiment;

DETAILED DESCRIPTION OF THE PREFERRED EMBODIMENT(S)

Figure 3:
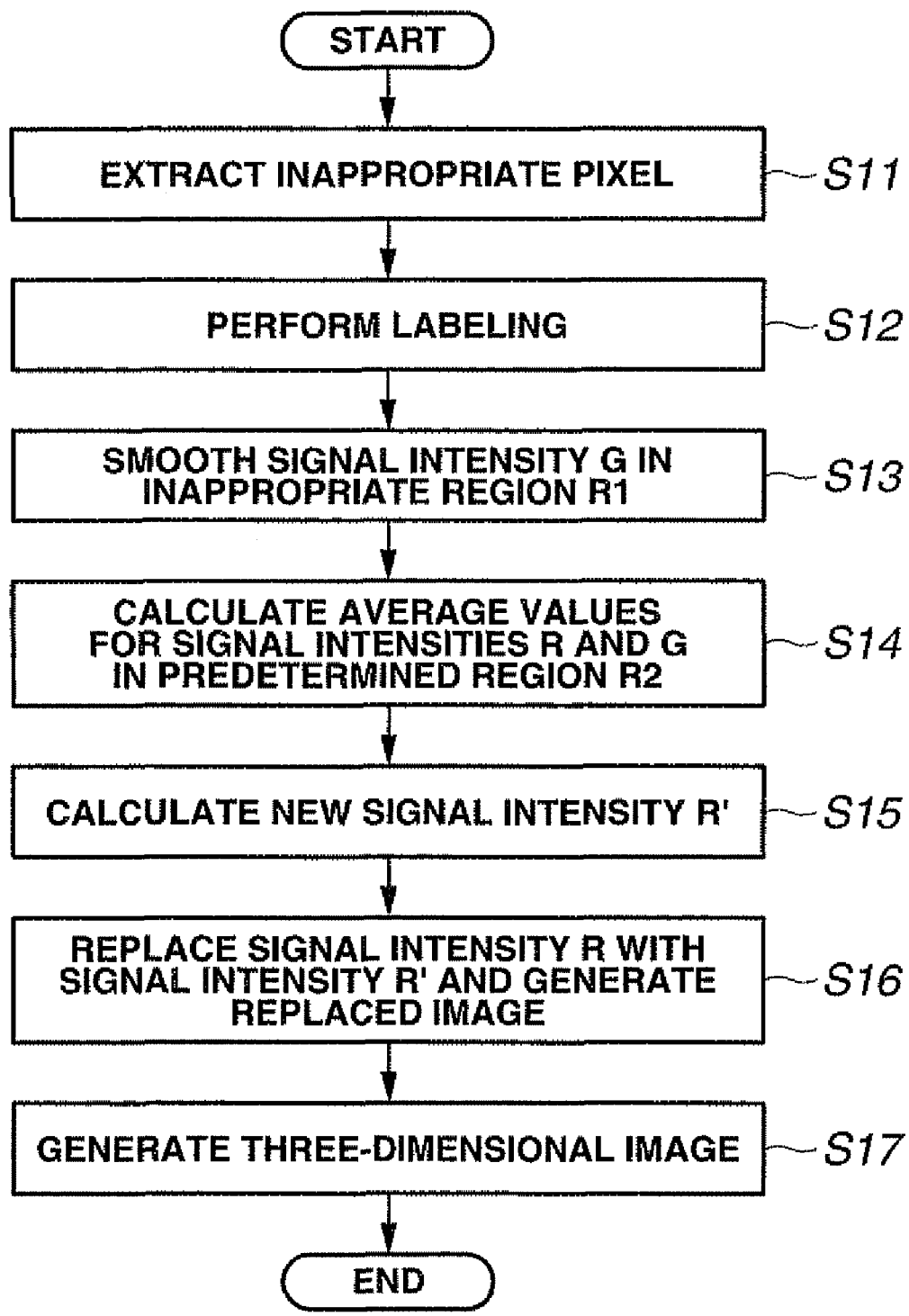
FIG. 3 is a flow chart for an example of a flow of image processing in the image processing apparatus according to the first embodiment.

Embodiments of the present invention will be described below.

An image processing apparatus according to an embodiment of the present invention extracts, e.g., a halation pixel, a pixel in which only an R signal intensity value is saturated (hereinafter referred to as an R saturated pixel), a missing pixel, or the like present in an inputted medical image. The image processing apparatus is capable of calculating new pixel information based on pixel information such as a signal intensity value of a portion around the pixel and generating an image obtained by replacing pixel information of the pixel with the calculated pixel information.

That is, the image processing apparatus is configured to be capable of altering, e.g., the halation pixel, R saturated pixel, missing pixel, or the like included in an input image to a pixel suitable for three-dimensional image generation processing.

An image processing apparatus according to a first embodiment will be described first.

First Embodiment

An image processing apparatus according to a first embodiment will be described below.

Medical images have recently been subjected to a process of converting a two-dimensional image into a three-dimensional image to find a lesioned part. Such a three-dimensional image is generated by adding, to each of pixels constituting a two-dimensional picked-up image, three-dimensional coordinates based on luminance of each of the pixels.

Methods for generating a three-dimensional image include a method for converting a coordinate system of two-dimensional endoscope image into a coordinate system defining a Z direction as a luminal direction and a θ direction as a circumferential direction which takes a position of a darkest portion in the two-dimensional endoscope image as a center position and generating a developed view. For the reason, three-dimensional coordinates of a pixel such as a halation pixel, R saturated pixel, or missing pixel which has abnormal luminance may significantly deviate from values supposed to be obtained.

An image processing apparatus of the present embodiment is configured to be capable of altering a halation pixel or the like included in an input image to a pixel suitable for three-dimensional image generation processing and generating a three-dimensional image based on an altered image. Note that an R saturated pixel will be referred to as an inappropriate pixel in a following description.

An image processing apparatus according to the present embodiment will first be described below.

FIG. 1 is a diagram of a schematic configuration of the image processing apparatus according to the present embodiment. As shown in FIG. 1, an image processing apparatus 1 is composed of an extraction portion 2, a calculation portion 3, a replacement portion 4, and a three-dimensional image generation portion 5. The extraction portion 2, calculation portion 3, replacement portion 4, and three-dimensional image generation portion 5 each has a plurality of electronic devices including a CPU.

The extraction portion 2 as pixel extraction means extracts an inappropriate pixel included in an input image. The calculation portion 3 as replacing pixel information calculation means calculates replacing information with which pixel information at the extracted inappropriate pixel is to be replaced. The replacement portion 4 as replaced image output means generates a replaced image obtained by replacing the pixel information at the inappropriate pixel with the calculated replacing information. The three-dimensional image generation portion 5 as three-dimensional image generation means generates a three-dimensional image based on the generated replaced image.

An input image inputted to the image processing apparatus 1 is a picked-up image picked up by an endoscope apparatus 6 having a CCD camera and the like. The picked-up image is an endoscope image obtained by picking up an image of an interior of a body cavity such as a large intestine and is composed of R, G, and B color signals. The color signals have a red signal intensity value R, a green signal intensity value G, and a blue signal intensity value B as pieces of pixel information.

FIG. 2 shows an example of a relationship between R, G, and B signal intensities at a certain row (or a certain column) of a two-dimensional x-y picked-up image and a pixel position. In FIG. 2, an ordinate axis represents a signal intensity while an abscissa axis represents a pixel position at a certain row (or a certain column) in a picked-up image, e.g., along an x direction (or a y direction).

As shown in FIG. 2, in an inputted picked-up image, a ratio among a red signal intensity value R, a green signal intensity value G, and a blue signal intensity value B is almost same at pixels.

Since absorption of light in a living mucous membrane on a surface of an interior of a body cavity depends on the amount of hemoglobin bound to oxygen, a red signal intensity value R is highest. For the reason, only red signal intensity value R is saturated in some living mucous membrane images.

This means that a pixel whose red signal intensity value R is saturated shown in FIG. 2, e.g., a pixel having a signal intensity of not less than 255, is an inappropriate pixel.

The image processing apparatus 1 extracts such an inappropriate pixel included in a picked-up image, calculates replacing information with which pixel information at the inappropriate pixel is to be replaced, and generates a three-dimensional image based on a replaced image generated by replacing the pixel information at the inappropriate pixel with the calculated replacing information.

Details of the image processing in the image processing apparatus 1 will be described with reference to FIGS. 2 and 3. FIG. 3 is a flow chart for an example of a flow of the image processing in the image processing apparatus 1. A process to be described below starts when a picked-up image is inputted to the image processing apparatus 1.

First, the image processing apparatus 1 extracts inappropriate pixels in the inputted picked-up image (step S11). The extraction of the inappropriate pixels is performed by the extraction portion 2.

Pixels of the two-dimensional picked-up image are sequentially scanned from, e.g., a pixel (1, 1), and it is determined whether or not a red signal intensity value Rij (i, j: coordinates of a pixel in the picked-up image) is equal to or more than a predetermined threshold value, thereby extracting the inappropriate pixels.

In the present embodiment, the predetermined threshold value is a signal intensity value of 255, and a pixel whose red signal intensity value Rij shown in FIG. 2 is not less than 255 is determined as an inappropriate pixel. Note that the predetermined threshold value may be set to a value depending on an inappropriate pixel desired to be extracted.

The image processing apparatus 1 labels the extracted inappropriate pixels (step S12). The labeling is performed by the extraction portion 2.

By the labeling, the two-dimensional picked-up image is scanned sequentially from, e.g., the pixel (1, 1), and a same attribute such as a number, i.e., a same label is attached to adjacent inappropriate pixels.

A label having a different value is assigned to each region composed of a plurality of inappropriate pixels. Further processing is performed for each of the labeled regions. A region composed of a plurality of inappropriate pixels will be referred to as an inappropriate region hereinafter.

In FIG. 2, a region composed of inappropriate pixels, each of which has a red signal intensity value Rij of not less than 255, is shown as an inappropriate region R1. A same label is attached to the inappropriate pixels constituting the inappropriate region R1.

The image processing apparatus 1 smoothes a green signal intensity value Gij of each pixel in the inappropriate region R1 and calculates a smoothed signal intensity value Gs which is a smoothed signal intensity (step S13). The smoothing is performed by the calculation portion 3. Step S13 constitutes smoothing means.

The smoothing is a process of sequentially replacing the green signal intensity value Gij at an object pixel as which each of the inappropriate pixels belonging to the inappropriate region is regarded with, e.g., an average value of signal intensity values within a range of eight surrounding pixels.

Other methods for the smoothing include a neighboring weighted average method and a median method, and any method may be used. A range for average value calculation in the smoothing is not limited to a range of eight surrounding pixels and can be freely changed depending on a desired smoothing degree.

The smoothing is sequentially performed on the inappropriate pixels belonging to each of the labeled inappropriate regions. In FIG. 2, object pixels to be subjected to the smoothing are Gij in the inappropriate region R1.

The image processing apparatus 1 calculates an average value ($\mu\_R$) for a red signal intensity value R as a first average signal intensity value and an average value ($\mu\_G$) for a green signal intensity value G as a second average signal intensity value in a predetermined region (step S14). The average values are calculated by the calculation portion 3. Step S14 constitutes averaging means.

The predetermined region is a region which includes at least one pixel adjacent to an inappropriate region with an object label and is composed of pixels that are not inappropriate pixels. The region is composed of a possible maximum number of pixels (e.g., 5×5 pixels). That is, the predetermined region is a region in a neighborhood of an inappropriate region which is tangent to pixels belonging to the inappropriate region. A size of the predetermined region is not limited to 5×5 pixels and can be freely changed depending on an inputted picked-up image.

FIG. 2 shows a predetermined region R2. The average value ($\mu\_R$) for a red signal intensity value R and the average value ($\mu\_G$) for a green signal intensity value G are calculated based on red signal intensity values Rij and green signal intensity values Gij, in the predetermined region R2, respectively.

The image processing apparatus 1 calculates a red signal intensity value R'ij as replacing information for each inappropriate pixel belonging to the inappropriate regions (step S15). The red signal intensity value R'ij is calculated by the calculation portion 3. Step S15 constitutes replacing information calculation means.

As described above, a ratio between a red signal intensity value R and a green signal intensity value G is almost same at pixels constituting a picked-up image. For the reason, assuming that a ratio between the red signal intensity value R'ij and the corresponding smoothed signal intensity value Gs in the inappropriate region is almost same as a ratio between the average value ($\mu\_R$) and the average value ($\mu\_G$) calculated for the region in a neighborhood of the inappropriate region, the red signal intensity value R'ij is calculated based on a formula (1) below.

$$R'ij = Gsij \times [(\mu\_R)/(\mu\_G)] \quad (1)$$

As shown in the formula (1), the red signal intensity value R'ij in the inappropriate region is calculated by multiplying a smoothed signal intensity Gsij by the ratio between the average value ($\mu\_R$) and the average value ($\mu\_G$).

The image processing apparatus 1 sequentially replaces the red signal intensity value Rij of each of the inappropriate pixels belonging to each inappropriate region with the calculated red signal intensity value R'ij and generates a replaced image (step S16). The processing is performed by the replacement portion 4. Step S16 constitutes replaced image output means.

Finally, the image processing apparatus 1 generates a three-dimensional image based on the replaced image (step S17). The processing is performed by the three-dimensional image generation portion 5. Step S17 constitutes three-dimensional image generation means.

Note that steps S11 and S12 constitute a pixel extraction step. Also note that steps S13 to S15 constitute a replacing pixel information calculation step. Step S16 constitutes a replaced image output step.

As has been described above, the image processing apparatus 1 of the present embodiment is capable of calculating and replenishing image data of a portion from which an accurate image processing result is not obtained and outputting a three-dimensional image. That is, the image processing apparatus 1 is capable of altering an inappropriate pixel (R saturated pixel) included in an input image to a pixel suitable for three-dimensional image generation processing and generating a three-dimensional image based on an altered image.

Note that although the image processing apparatus 1 of the present embodiment smoothes a green signal intensity value G and calculates a corresponding smoothed signal intensity value Gs in step S13 of FIG. 2, a blue signal intensity value B may be smoothed, and a corresponding smoothed signal intensity value Bs may be calculated. This is because a ratio among a red signal intensity value R, a green signal intensity value G, and a blue signal intensity value B is almost same at pixels, as described above.

Although the average value ($\mu\_G$) for a green signal intensity G is calculated in step S14, an average value ($\mu\_B$) for a blue signal intensity B may be calculated for similar reasons. Note that smoothed signal intensity values and an average value for a signal intensity calculated in steps S13 and S14 need to be calculated for the same color signal.

Second Embodiment

A second embodiment will now be described below.

An image processing apparatus according to the second embodiment will be described below. The image processing apparatus of the present embodiment is different from the one in the first embodiment and is configured to be capable of altering not only an R saturated pixel included in an input image but also a halation pixel and a missing pixel to pixels suitable for three-dimensional image generation processing and generating a three-dimensional image based on an altered image. Note that the R saturated pixel, the halation pixel, and the missing pixel will be referred to as the inappropriate pixels in a following description.

The image processing apparatus according to the present embodiment has a same configuration as the image processing apparatus according to the first embodiment. Same components will be denoted by the same reference numerals, and a description of the components will be omitted. As in the first embodiment, a picked-up image inputted to an image processing apparatus 1 is an endoscope image of, e.g., a large intestine picked up by an endoscope apparatus 6.

Figure 4:
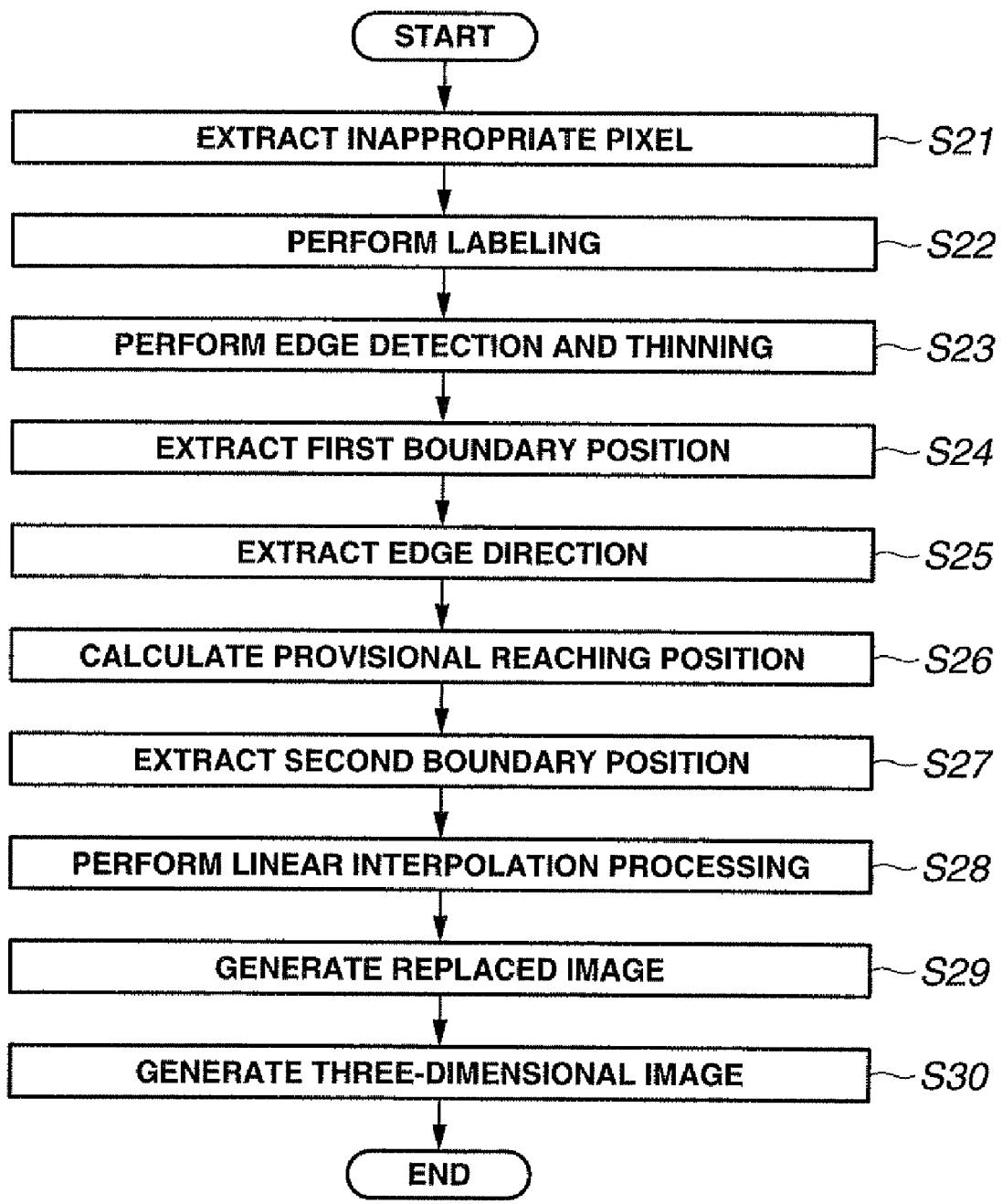
FIG. 4 is a flow chart for an example of a flow of image processing in an image processing apparatus according to a second embodiment.
Figure 5:
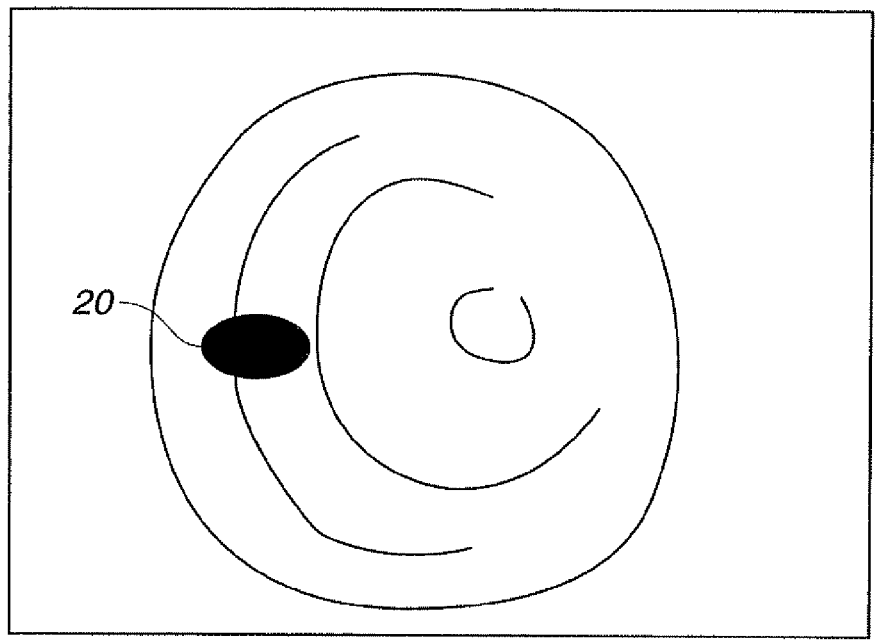
FIG. 5 is a schematic view of an example of an edge image according to the second embodiment.

Details of image processing in the image processing apparatus 1 of the present embodiment will be described with reference to FIGS. 4 to 10. FIG. 4 is a flow chart for an example of a flow of the image processing in the image processing apparatus 1 of the present embodiment. FIG. 5 is a schematic view of an example of a generated edge image. FIGS. 6 to 10 are enlarged views of an inappropriate region and a neighborhood.

Note that a process to be described below starts when a picked-up image is inputted to the image processing apparatus 1.

First, the image processing apparatus 1 extracts the inappropriate pixels in the inputted picked-up image (step S21). As described above, inappropriate pixels to be extracted include the R saturated pixel, halation pixel, and missing pixel. The extraction of the inappropriate pixels is performed by an extraction portion 2.

Pixels of the two-dimensional picked-up image are sequentially scanned from, e.g., a pixel (1, 1), and a pixel in which a signal intensity value of any color signal is not less than a predetermined first threshold value or a pixel in which signal intensity values of all color signals are not more than a predetermined second threshold value is determined as an inappropriate pixel, thereby extracting the inappropriate pixels.

The predetermined first threshold value is a signal intensity value of 255, and a pixel whose red signal intensity value is not less than 255 is the R saturated pixel or halation pixel and is determined as the inappropriate pixel. The predetermined second threshold value is a signal intensity value of 0, and a pixel in which signal intensity values of all color signals are not more than 0 is a missing pixel and is determined as an inappropriate pixel. The first threshold value and second threshold value are not limited to the above-described values and can be freely changed depending on an inappropriate pixel desired to be extracted.

Next, the image processing apparatus 1 labels the extracted inappropriate pixels (step S22). The labeling is performed by the extraction portion 2.

The labeling is a process of sequentially scanning the pixels of the two-dimensional picked-up image from, e.g., the pixel (1, 1) and attaching a same attribute such as a number, i.e., a same label to adjacent inappropriate pixels.

A label to be attached has a value different for each region composed of a plurality of inappropriate pixels. Further processing is performed for each of the labeled regions. The region composed of a plurality of inappropriate pixels will be referred to as an inappropriate region hereinafter.

The image processing apparatus 1 performs edge detection and thinning on the color signals constituting the inputted picked-up image and generates an edge image (step S23). The edge detection and thinning is performed by a calculation portion 3. Step S23 constitutes edge image generation means.

By the edge detection, a pixel in the inputted picked-up image at which brightness of each color signal drastically changes is detected as an edge. Based on a result of the detection, an edge image which is a binary image obtained by setting the pixels as detected edge portions to have a signal value of "1" and the other pixels to have a signal value of "0" is generated.

Furthermore, the calculation portion 3 performs thinning, which is a process of altering an edge of a generated edge image to a continuous thin line having, e.g., a one-pixel width. Note that a method used for the edge detection and thinning processing may be any method.

FIG. 5 shows an example of the generated edge image. As shown in FIG. 5, an inner wall of a lumen in an inputted picked-up image is detected as the edges. The edge image includes an inappropriate region 20.

The image processing apparatus 1 extracts a first boundary position at which the edge is tangent to an inappropriate region (step S24). The extraction of the first boundary position is performed by the calculation portion 3. Step S24 constitutes first boundary position extraction means.

Figure 6:
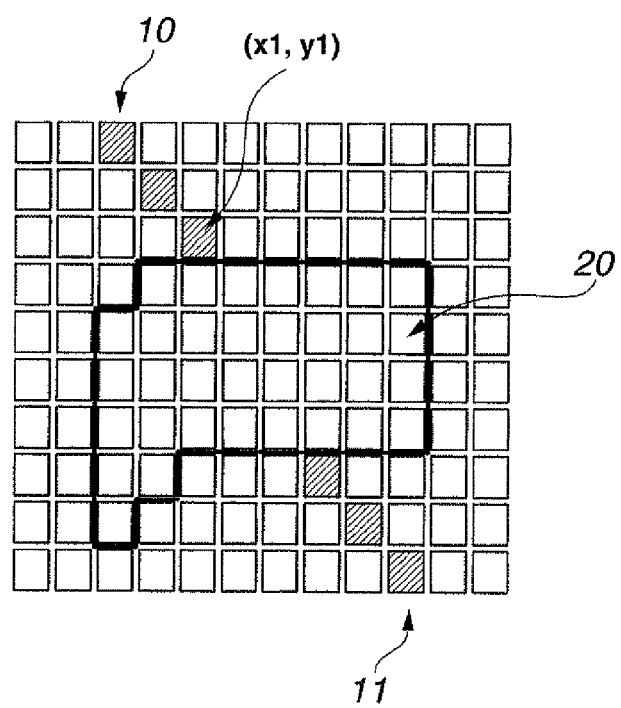
FIG. 6 is an enlarged view of an inappropriate region and a neighborhood showing a first boundary position according to the second embodiment.
Figure 7:
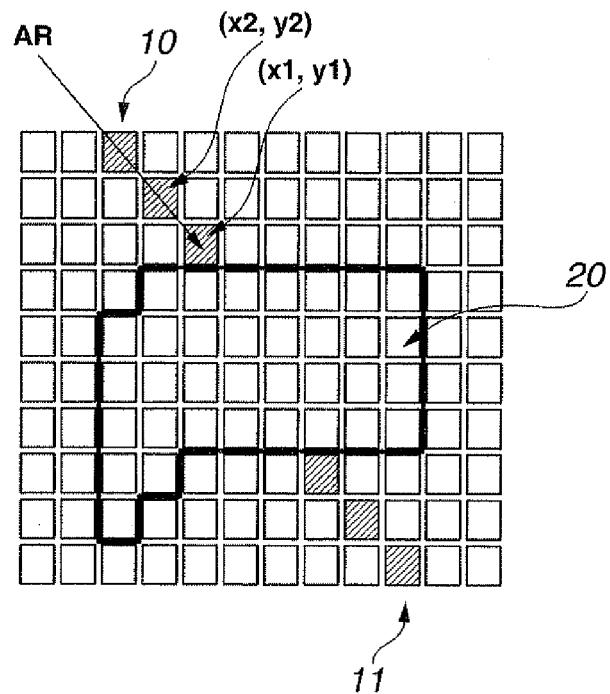
FIG. 7 is an enlarged view of the inappropriate region and neighborhood showing an edge direction according to the second embodiment.

A first boundary position is a position of a pixel at which a certain edge is tangent to an inappropriate region. FIG. 6 shows an enlarged view of the inappropriate region 20 and a neighborhood. In FIG. 6, one square corresponds to one pixel. A shaded pixel has a signal of "1" and represents the edge while a plain pixel is a pixel having a signal of "0". A pixel portion surrounded by a thick line indicates the inappropriate region 20.

As shown in FIG. 6, an edge 10 and an edge 11 are tangent to the inappropriate region 20. A position of a pixel (x1, y1) at which the edge 10 is tangent to the inappropriate region 20 is the first boundary position.

The image processing apparatus 1 extracts an edge direction (step S25). The extraction of the edge direction is performed by the calculation portion 3. Step S25 constitutes edge direction extraction means.

First, a pixel which is tangent to the pixel at the first boundary position and is not tangent to the inappropriate region is detected. Assuming that the position of the pixel is (x2, y2), the edge direction is calculated by (x1−x2, y1−y2). The edge direction is indicated by an arrow AR in FIG. 7.

After the edge direction is extracted, the image processing apparatus 1 calculates a provisional reaching position based on the first boundary position and edge direction (step S26). The calculation of the provisional reaching position is performed by the calculation portion 3. Step S26 constitutes provisional reaching position calculation means.

The provisional reaching position is a position where the edge first reaches after the edge is extended along the edge direction from the first boundary position into the inappropriate region 20 and crosses over the inappropriate region 20.

Figure 8:
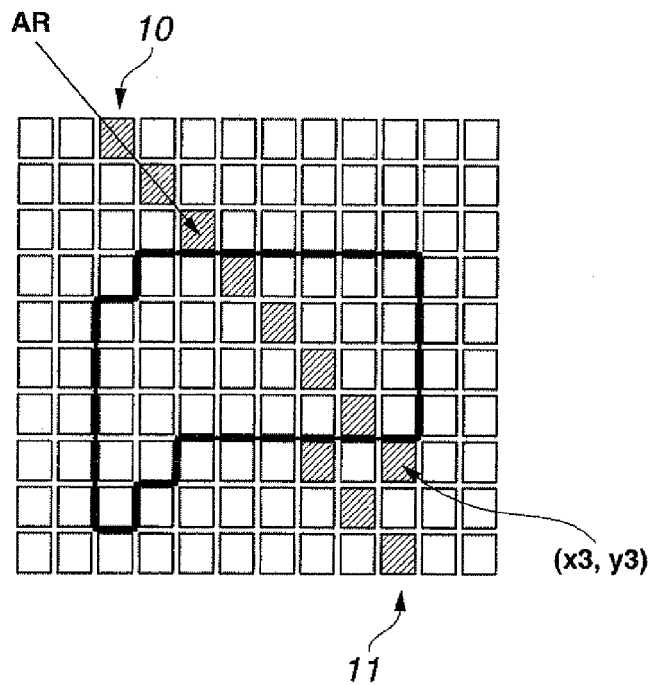
FIG. 8 is an enlarged view of the inappropriate region and neighborhood showing a position of a provisional reaching pixel according to the second embodiment.

FIG. 8 shows the provisional reaching position. As shown in FIG. 8, a position (x3, y3) where the edge 10 first reaches after the edge 10 is extended in a direction of the arrow AR serving as the edge direction from the first boundary position (x1, y1) and crosses over the inappropriate region 20 is the provisional reaching position.

Next, the image processing apparatus 1 extracts a second boundary position based on the provisional reaching position (step S27). The extraction of the second boundary position is performed by the calculation portion 3. Step S27 constitutes second boundary position extraction means.

The calculation portion 3 first detects whether or not there is a pixel constituting an edge other than the edge 10 within a range of, e.g., 3×3 pixels about the provisional reaching position, i.e., the edge 11. Note that the range for detection of the edge 11 is not limited to the range of 3×3 pixels and can be freely changed.

If there is a pixel constituting part of the edge 11, the calculation portion 3 determines that the edge 10 and edge 11 should be one continuous edge. The calculation portion 3 extracts a position of a pixel at which the edge 11 is tangent to the inappropriate region 20 as the second boundary position.

Figure 9:
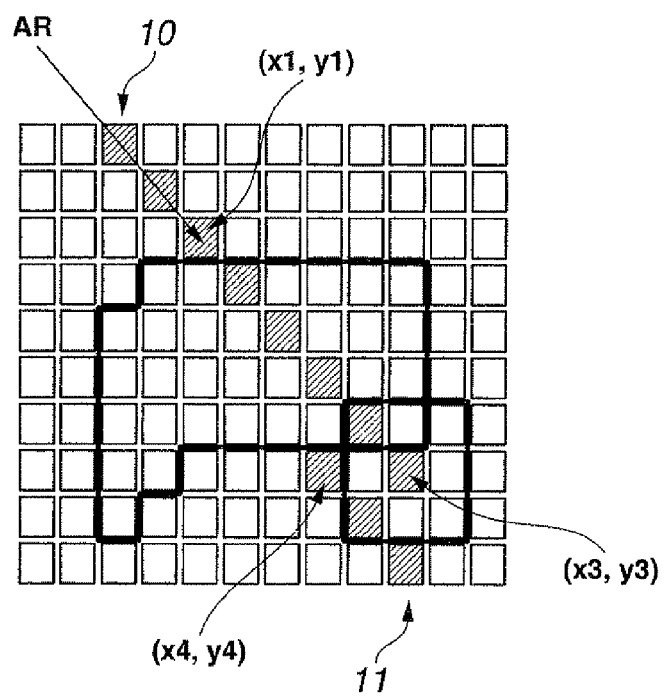
FIG. 9 is an enlarged view of the inappropriate region and neighborhood showing a second boundary position according to the second embodiment.

FIG. 9 shows the second boundary position. First, a pixel constituting part of the edge 11 within the range of 3×3 pixels about the provisional reaching position (x3, y3). A position of the detected pixel, at which the edge 11 is tangent to the inappropriate region 20, is the second boundary position (x4, y4).

Note that if the second boundary position (x4, y4) is not present within a range of, e.g., 5×5 pixels about the provisional reaching position (x3, y3), the calculation portion 3 determines that the edge 10 and edge 11 are not continuous with each other and that there is no edge in the inappropriate region 20.

If there is no pixel constituting part of the edge within a detection range of, e.g., 3×3 pixels about the provisional reaching position (x3, y3), the calculation portion 3 determines that there is no edge in the inappropriate region 20 and performs processing on a next labeled inappropriate region.

The image processing apparatus 1 performs linear interpolation processing on a path between the first boundary position and the second boundary position and calculates a new signal value of each pixel in the path (step S28). The linear interpolation processing is performed by the calculation portion 3. Step S28 constitutes replacing information calculation means.

The linear interpolation processing is a process of weighting a signal value of each of e.g., four pixels around a pixel to be processed according to a distance from the pixel to be processed and calculating a new signal value as replacing information.

The new signal values are calculated such that as much of a path obtained when the provisional reaching pixel is calculated in step S26 as possible is included, and a distance between the first boundary pixel and the second boundary pixel is shortest.

The image processing apparatus 1 generates a replaced image obtained by replacing pixel information of each pixel in the inappropriate region with a corresponding calculated new signal value (step S29). The generation of the replaced image is performed by the replacement portion 4. Step S29 constitutes replaced image generation means.

Figure 10:
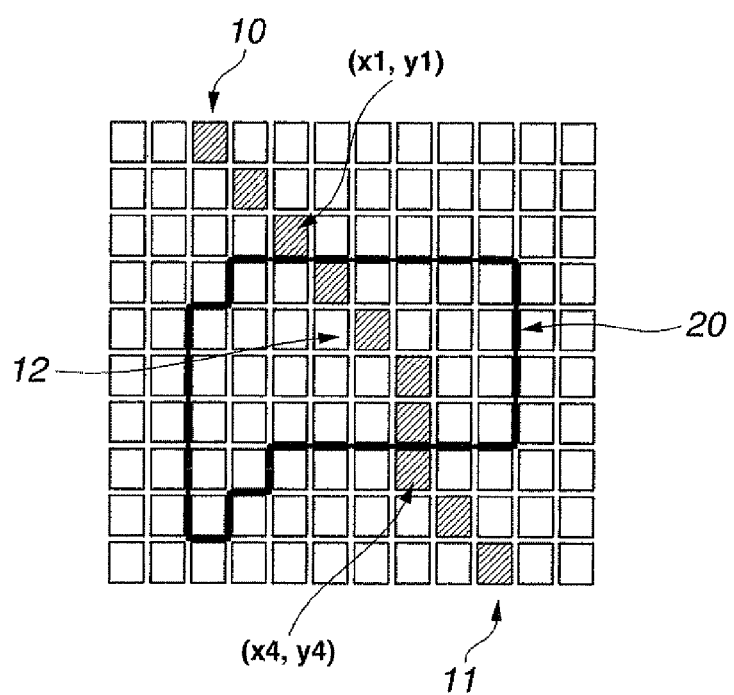
FIG. 10 is an enlarged view of the inappropriate region and neighborhood in a replaced image according to the second embodiment.

FIG. 10 shows an enlarged view of the inappropriate region 20 and neighborhood in the generated replaced image. As shown in FIG. 10, the new signal values calculated by the linear interpolation processing constitute an edge 12 in the path between the first boundary position (x1, y1) and the second boundary position (x4, y4). As a result, the edge 12 connects the edge 10 and the edge 11.

Finally, the image processing apparatus 1 generates a three-dimensional image based on the replaced image (step S30). The processing is performed by the three-dimensional image generation portion 5. Step S30 constitutes three-dimensional image generation means.

With that, the processing ends. The processes in steps S23 to S29 are performed for the respective color signals.

Note that steps S21 and S22 constitute a pixel extraction step. Also note that steps S23 to S28 constitute a replacing pixel information calculation step. Step S29 constitutes a replaced image output step.

As has been described above, the image processing apparatus 1 of the present embodiment is capable of calculating and replenishing image data of a portion from which an accurate image processing result is not obtained and outputting a three-dimensional image. That is, the image processing apparatus 1 is capable of altering the R saturated pixel, the halation pixel, and the missing pixel included in the input image to pixels suitable for three-dimensional image generation processing and generating a three-dimensional image based on the altered image.

Note that, in the present embodiment, three-dimensional image generation processing may first be performed, and the pixel extraction step, the replacing pixel information calculation step, and the replaced image output step may then be performed.

In the present embodiment, as for pixels other than the pixels as the edges in the inappropriate region, a signal value of each pixel is calculated using, e.g., a known polynomial operation method as disclosed in the specification of U.S. Patent Application Publication No. 2005/0001832, and replacement with the signal value is performed.

Incidentally, a picked-up image inputted to the image processing apparatus 1 in each of the first and second embodiments is an endoscope image picked up by the endoscope apparatus 6 as described above. In recent years, methods for finding a lesioned part such as polyp from such endoscope images by image processing have been used. Since the image processing apparatus 1 of each of the above-described embodiments is capable of generating a replaced image obtained by replacing inappropriate pixels, the image processing apparatus 1 is effective in performing image processing for finding such a lesioned part.

Figure 11:
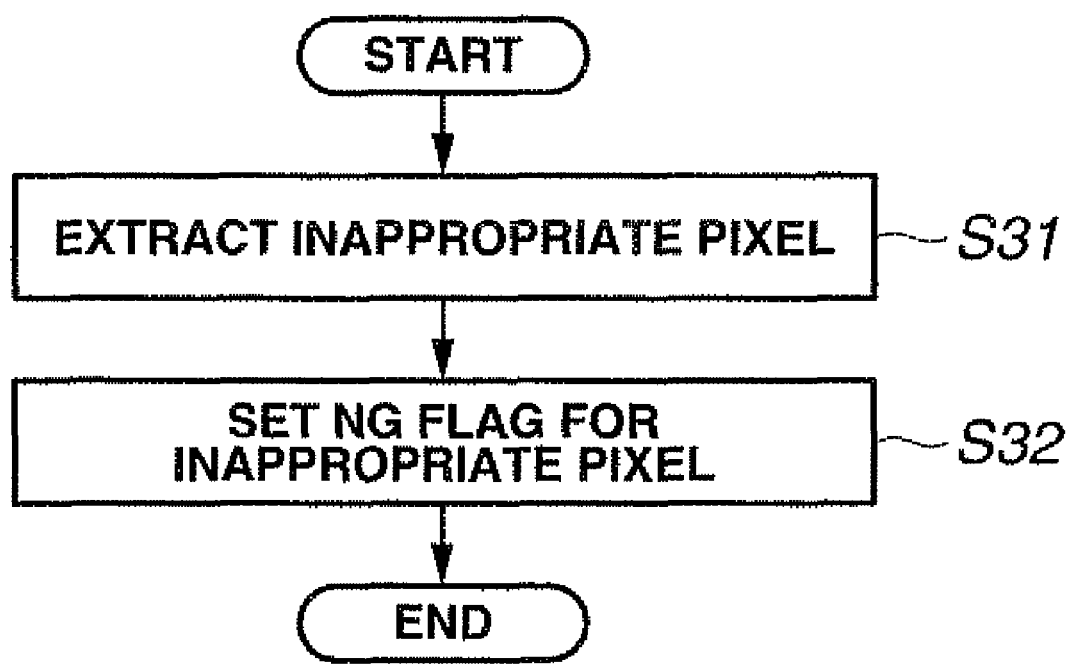
FIG. 11 is a flow chart showing a flow of a modification example of the image processing according to the embodiments of the present invention.

At this time, the image processing apparatus 1 of each of the first and second embodiments may perform processing as shown in FIG. 1. FIG. 11 is a flow chart showing a flow of a modification example of the image processing according to the embodiments of the present invention. A process to be described below starts when a picked-up image is inputted to the image processing apparatus 1.

First, the image processing apparatus 1 extracts inappropriate pixels (step S31). In the step, inappropriate pixels included in the inputted picked-up image are extracted, as in the first and second embodiments described above.

Next, the image processing apparatus 1 sets an NG flag for each of the extracted inappropriate pixels (step S32). For example, an NG flag is set to "1" for each inappropriate pixel such that the pixel is excluded from the three-dimensional image generation processing performed in the three-dimensional image generation portion 5.

With that, the processing ends. The processing makes it possible to eliminate an influence of an inappropriate pixel in the three-dimensional image generation processing in the three-dimensional image generation portion 5.

As has been described above the image processing apparatus 1 according to the present embodiments of the present invention is capable of calculating and replenishing image data of a part from which an accurate image processing result is not obtained. That is, the image processing apparatus 1 is capable of altering the R saturated pixel, the halation pixel, the missing pixel, and the like included in the input image to pixels suitable for the three-dimensional image generation processing.

Note that, in the embodiments of the present invention, if a ratio of inappropriate pixels to all the pixels constituting the input image is not less than a certain level, the input image may be determined to possess low reliability, and the input image may not be subjected to processing.

In the embodiments of the present invention, the three-dimensional image generation portion 5 of the image processing apparatus 1 may perform a different image processing. Furthermore, the three-dimensional image generation portion 5 may be provided outside the image processing apparatus 1. That is, since the image processing apparatus 1 is capable of altering an input image including an inappropriate pixel to an image suitable for image processing, the image processing apparatus 1 can be applied to any image processing.

Note that although the image processing apparatus 1 of each of the embodiments of the present invention is an apparatus different from the endoscope apparatus 6, the image processing apparatus 1 may be provided inside the endoscope apparatus 6.

Although the extraction portion 2, the calculation portion 3, the replacement portion 4, and the three-dimensional image generation portion 5 in each embodiment of the present invention have different configurations, one image processing portion or the like may perform the above-described processing.

In each embodiment of the present invention, a picked-up image inputted to the image processing apparatus 1 is picked up by the endoscope apparatus 6. However, a picked-up image obtained using different image pickup means may be adopted.

As has been described above, according to a medical image processing apparatus and a medical image processing method of the present invention, it is possible to calculate and replenish image data of a part from which an accurate image processing result is not obtained.

Note that the present invention is not limited to the above-described embodiments, and modifications can be made without departing from the scope of the present invention.

What is claimed is:

1. A medical image processing apparatus which performs image processing on a medical input image, comprising:
   pixel extraction means for extracting an inappropriate pixel satisfying a predetermined condition in the input image;
   replacing pixel information calculation means for calculating replacing information with which pixel information of the inappropriate pixel is to be replaced, based on pixel information of a predetermined region including the extracted inappropriate pixel or adjacent to the extracted inappropriate pixel; and
   replaced image generation means for replacing the pixel information of the inappropriate pixel in the input image with the replacing information and generating a replaced image, wherein:
   the input image is an RGB image;
   the inappropriate pixel satisfying the predetermined condition is a pixel in which a signal intensity value of an R signal is not less than a predetermined threshold value; and
   the pixel information comprises signal intensity values of R, G, and B signals; and
   wherein the replacing pixel information calculation means comprises:
      smoothing means for smoothing a signal intensity value of a G signal or a B signal at the extracted inappropriate pixel and calculating a smoothed signal intensity value;
      averaging means for obtaining a first average signal intensity value which is an average value for a signal intensity value of the R signal and a second average signal intensity value which is an average value for a signal intensity value of the G signal or the B signal, in the predetermined region adjacent to the extracted inappropriate pixel; and
      replacing information calculation means for calculating the replacing information based on the smoothed signal intensity value, the first average signal intensity value, and the second average signal intensity value.

2. The medical image processing apparatus according to claim 1, wherein
   the inappropriate pixel satisfying the predetermined condition is positioned in an inappropriate pixel region which is composed of a plurality of inappropriate pixels, and the inappropriate pixels in the inappropriate pixel region are each a pixel whose signal intensity value is not less than a first threshold value or is not more than a second threshold value that is smaller than the first threshold value, and
   the pixel information comprises a position and a signal value of a pixel constituting part of an edge in an edge image which is obtained by subjecting the input image to edging processing.

3. The medical image processing apparatus according to claim 2, wherein
   the replacing pixel information calculation portion comprises:
   a edge image generation portion for subjecting the input image to edging processing and generating the edge image;
   a first boundary position extraction portion for extracting a first boundary position at which the edge is tangent to the inappropriate pixel region;
   a edge direction extraction portion for extracting a direction of the edge;
   a provisional reaching position calculation portion for extending the edge from the first boundary position into the inappropriate pixel region based on the direction of the edge and calculating a provisional reaching position which the extended edge reaches just after the edge crosses the inappropriate pixel region and which is adjacent to the inappropriate pixel region;
   a second boundary position extraction portion for detecting an edge which is different from the edge in a predetermined region including the provisional reaching position and extracting a second boundary position at which the different edge is tangent to the inappropriate pixel region; and
   a replaced information calculation portion for calculating the replacing information based on the first boundary position and the second boundary position.

4. The medical image processing apparatus according to claim 1, further comprising a three-dimensional image generation portion for generating a three-dimensional image based on the generated replaced image.

5. A medical image processing method for performing image processing on a medical input image, comprising:
   a pixel extraction step of extracting an inappropriate pixel satisfying a predetermined condition in the input image;
   a replacing pixel information calculation step of calculating replacing information with which pixel information of the inappropriate pixel is to be replaced, based on pixel information of a predetermined region including the extracted inappropriate pixel or adjacent to the extracted inappropriate pixel; and
   a replaced image generation step of generating a replaced image obtained by replacing the pixel information of the inappropriate pixel in the input image with the calculated replacing information, wherein:
   the input image is an RGB image;
   the inappropriate pixel satisfying the predetermined condition is a pixel in which a signal intensity value of an R signal is not less than a predetermined threshold value; and
   the pixel information comprises signal intensity values of R, G, and B signals; and
   wherein the replacing pixel information calculation step comprises:
      a smoothing step for smoothing a signal intensity value of a G signal or a B signal at the extracted inappropriate pixel and calculating a smoothed signal intensity value;
      an averaging step for obtaining a first average signal intensity value which is an average value for a signal intensity value of the R signal and a second average signal intensity value which is an average value for a signal intensity value of the G signal or the B signal, in the predetermined region adjacent to the extracted inappropriate pixel; and
      a replacing information calculation step for calculating the replacing information based on the smoothed signal intensity value, the first average signal intensity value, and the second average signal intensity value.

* * * * *